(12) United States Patent
Kim et al.

(10) Patent No.: US 12,622,835 B2
(45) Date of Patent: May 12, 2026

(54) DRIVING SYSTEM AND CONTROL METHOD FOR HYBRID GAIT REHABILITATION ROBOT

(71) Applicants: Foundation for Research and Business, Seoul National University of Science and Technology, Nowon-gu Seoul (KR); National Rehabilitation Center, Gangbuk-gu Seoul (KR)

(72) Inventors: Jung Yup Kim, Seocho-gu Seoul (KR); Jung Joon Kim, Nowon-gu Seoul (KR); Hyeong Sic Kim, Nowon-gu Seoul (KR); Seon Deok Eun, Songpa-gu Seoul (KR); Do Hoon Koo, Nam-gu Gwangju (KR); Hyun Ju Park, Seongbuk-gu Seoul (KR)

(73) Assignees: FOUNDATION FOR RESEARCH AND BUSINESS, SEOUL NATIONAL UNIVERSITY OF SCIENCE AND TECHNOLOGY, Seoul (KR); NATIONAL REHABILITATION CENTER, Seoul (KR)

( * ) Notice: Subject to any disclaimer, the term of this patent is extended or adjusted under 35 U.S.C. 154(b) by 972 days.

(21) Appl. No.: 17/763,765

(22) PCT Filed: Sep. 15, 2020

(86) PCT No.: PCT/KR2020/012406
§ 371 (c)(1),
(2) Date: Mar. 25, 2022

(87) PCT Pub. No.: WO2021/060759
PCT Pub. Date: Apr. 1, 2021

(65) Prior Publication Data

US 2022/0339053 A1 Oct. 27, 2022

(30) Foreign Application Priority Data

Sep. 27, 2019 (KR) ........................ 10-2019-0119284

(51) Int. Cl.
*A61H 1/02* (2006.01)
*G16H 20/30* (2018.01)
*G16H 40/63* (2018.01)

(52) U.S. Cl.
CPC ........... *A61H 1/0262* (2013.01); *G16H 20/30* (2018.01); *G16H 40/63* (2018.01);
(Continued)

(58) Field of Classification Search
CPC .......... A61H 1/0262; A61H 2201/1215; A61H 2201/1463; A61H 2201/1676;
(Continued)

(56) References Cited

U.S. PATENT DOCUMENTS 10,690,493 B2 * 6/2020 Roozeboom .............. G01P 3/54
2002/0198080 A1 * 12/2002 Reck .................. A63B 21/0058
482/8

FOREIGN PATENT DOCUMENTS

EP 0301605 * 2/1989 ........... A61H 1/0214
EP 0301605 B1 * 10/1991 ........... A61H 1/0214
(Continued)

OTHER PUBLICATIONS

EP0301605_Machine_Translation_Accessed_2_6_25 (Year: 2025).*
(Continued)

*Primary Examiner* — Victoria Murphy
*Assistant Examiner* — Kris Hanyu Gong
(74) *Attorney, Agent, or Firm* — Panitch Schwarze Belisario & Nadel LLP

(57) ABSTRACT

A driving system of a hybrid gait rehabilitation robot include: a driving unit that is connected to a footrest of the
(Continued)

gait rehabilitation robot and transmits a driving force such that the robot operates at a preset speed; a speed detection unit that detects a gait speed of an occupant; and a control unit that controls a speed of the driving unit by comparing the detected speed of the speed detection unit with a speed applied by the driving unit. The driving unit transmits power toward the occupant, but the driving force of the occupant is not transmitted to the driving unit.

4 Claims, 4 Drawing Sheets

(52) U.S. Cl.
CPC ................ *A61H 2201/1215* (2013.01); *A61H 2201/1463* (2013.01); *A61H 2201/1676* (2013.01); *A61H 2201/5058* (2013.01)

(58) Field of Classification Search
CPC ...... A61H 2201/5058; A61H 2201/149; A61H 2201/1642; A61H 2201/5007; A61H 2201/5079; A61H 2230/625; A61H 3/00; A61H 1/0214; G16H 20/30; G16H 40/63; A61B 5/00; A61B 5/11; A61B 5/22; A61B 5/112; A61B 5/1124; A61B 5/224; A61B 5/6887; A63B 23/04; A63B 24/00; A63B 24/0087; A63B 2024/0093; A63B 2220/30; A63B 2220/40; A63B 21/0058
See application file for complete search history.

(56) References Cited

FOREIGN PATENT DOCUMENTS

| | | | | |
|---|---|---|---|---|
| EP | 2564904 | A1 * | 3/2013 | ........... A61H 1/0214 |
| KR | 10-1424109 | B1 | 8/2014 | |
| KR | 10-1680740 | B1 | 11/2016 | |
| KR | 10-1939581 | B1 | 1/2019 | |
| KR | 10-2019-0046161 | A | 5/2019 | |

OTHER PUBLICATIONS

EP_0301605_machine_translation (Year: 2025).*

Int'l Search Report issued Feb. 4, 2021 in Int'l Application No. PCT/KR2020/012406.

Kim et al, "Development of an End-effector Typed Walking Rehabilitation Robot Capable of Power Assistance," Transactions of the Korean Society of Mechanical Engineers, vol. 42, No. 8, pp. 721-730 (2018).

J-Y Kim, et al., "Gait Training Algorithm of an End-Effector Typed Hybrid Walking Rehabilitation Robot," Int. J. Precis. Eng. Manuf. 20, 1767-1775 (2019).

J-J Kim, et al., "Power Assistance and Evaluation of an End-effector Typed Walking Rehabilitation Robot," 2018 18th International Conference on Control, Automation and Systems (ICCAS), PyeongChang, Korea (South), 2018, pp. 1353-1355.

* cited by examiner

【FIG. 1】
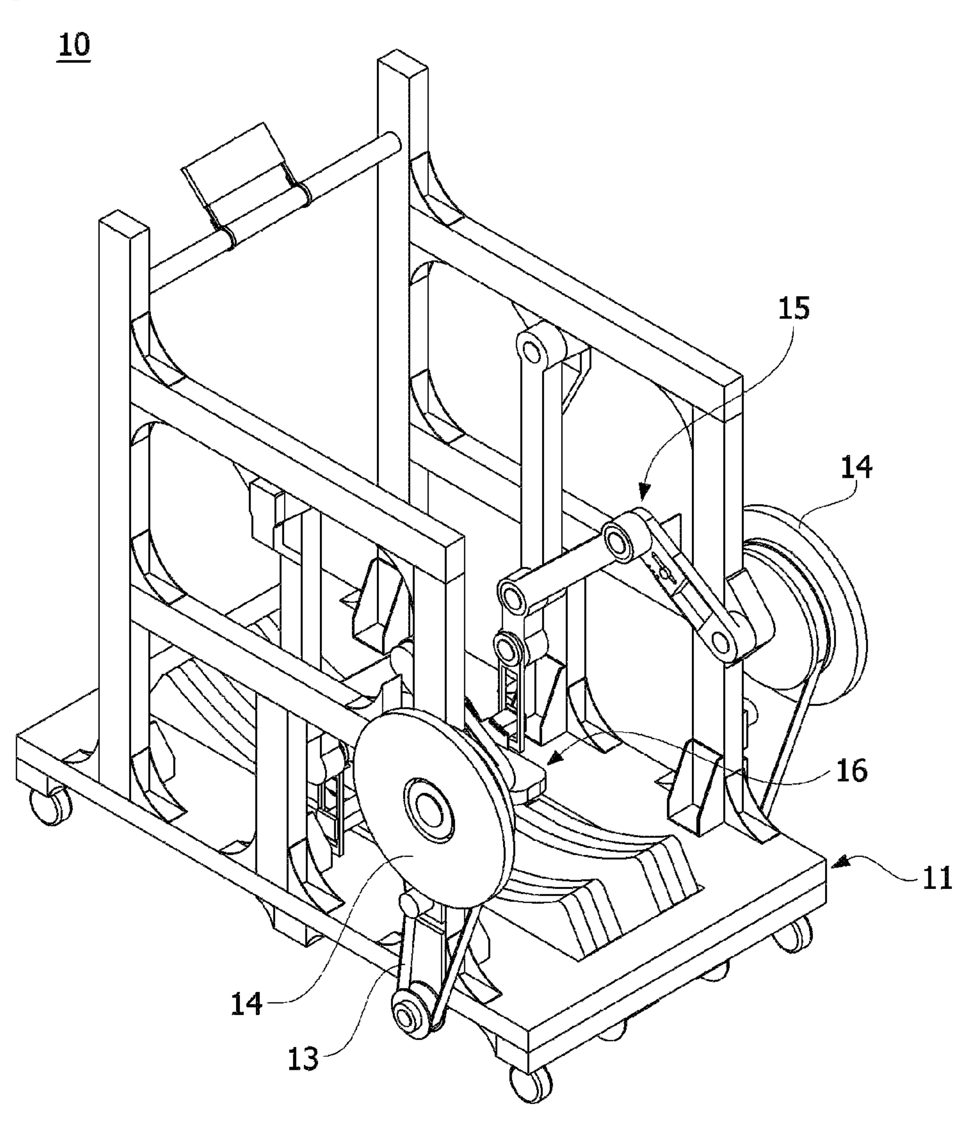

【FIG. 2】
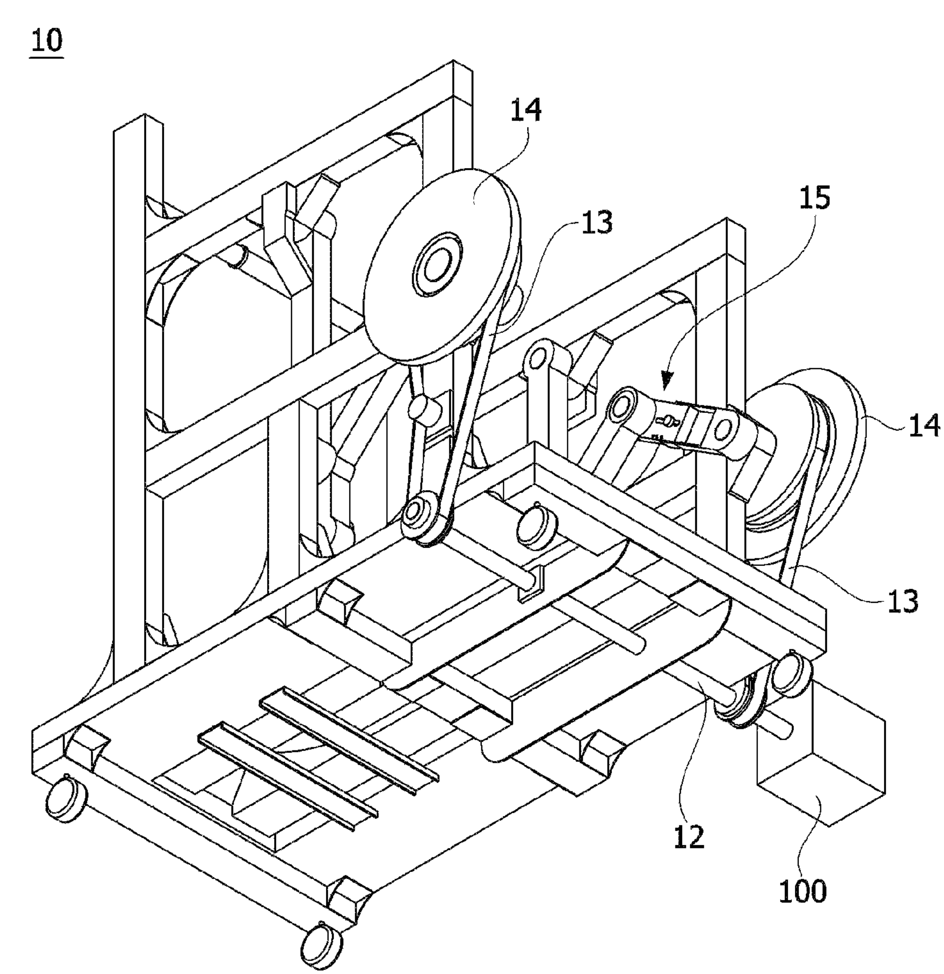
【FIG. 3】
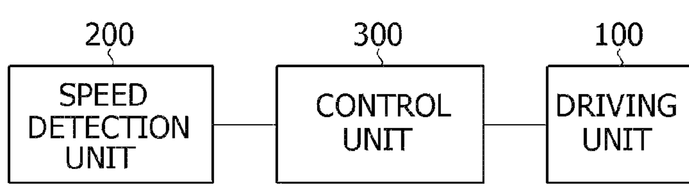
【FIG. 4】
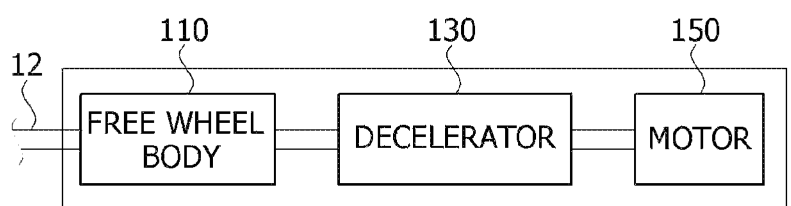

【FIG. 5】
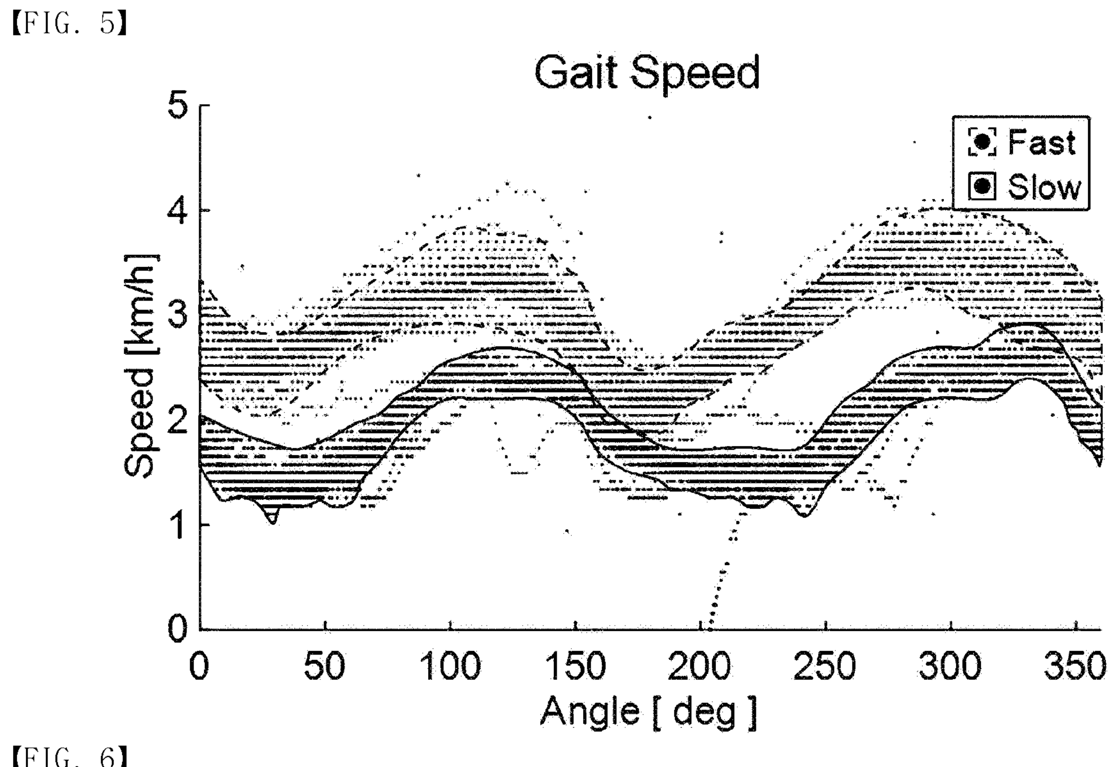
【FIG. 6】
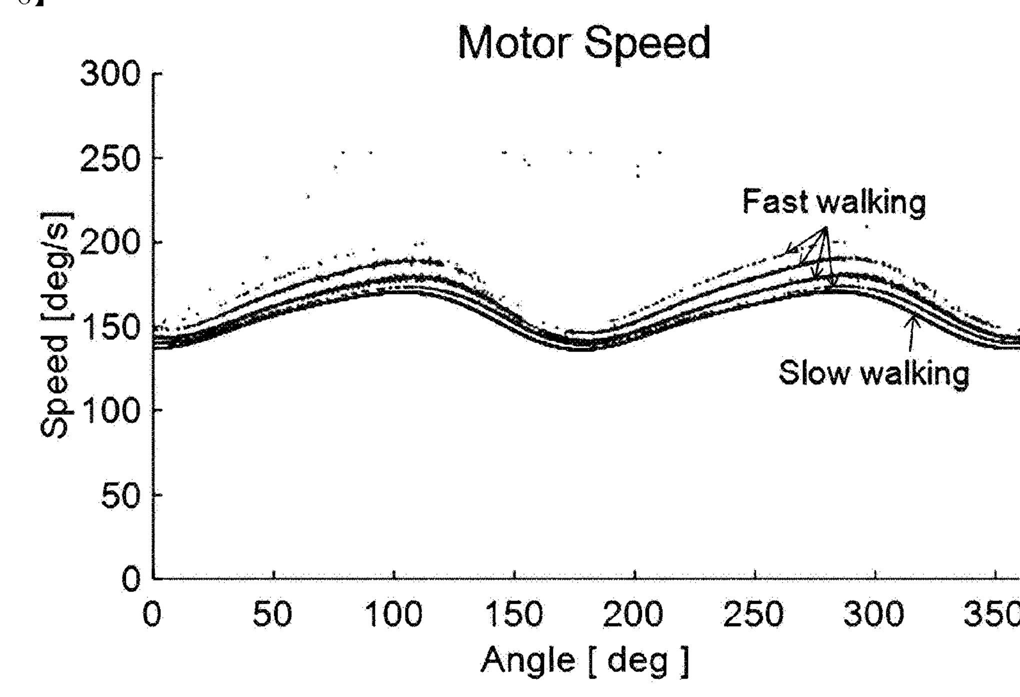

【FIG. 7】
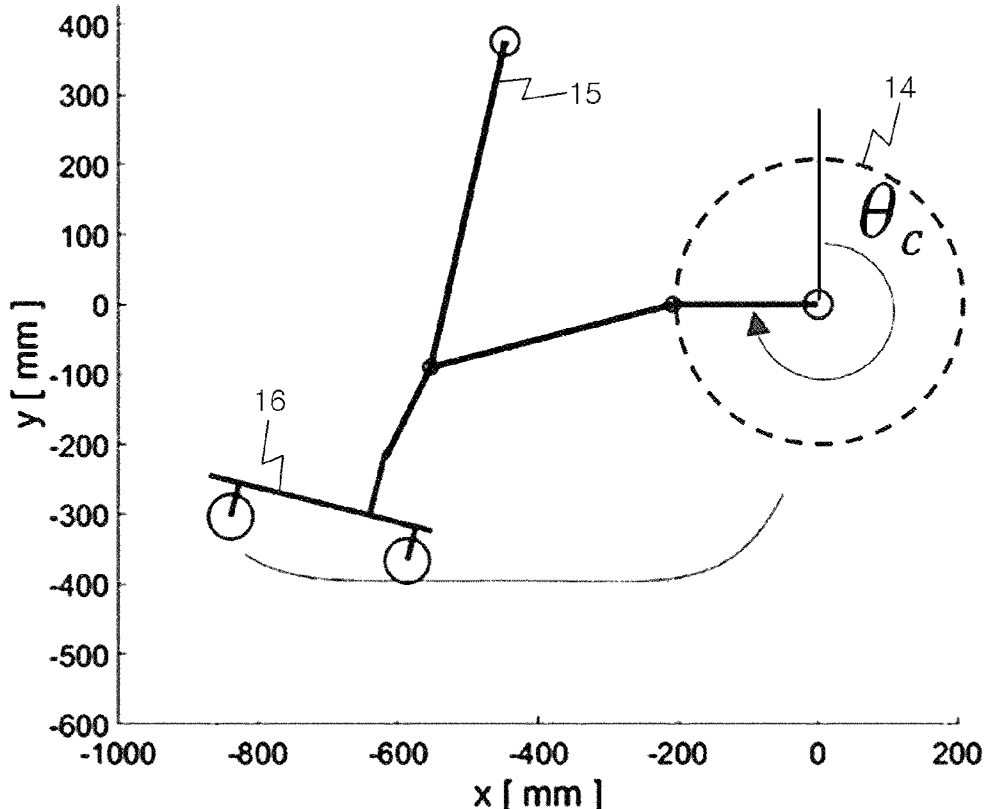
【FIG. 8】
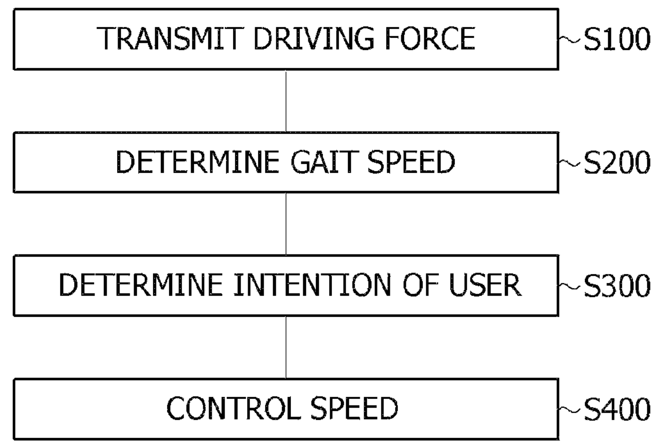

DRIVING SYSTEM AND CONTROL METHOD FOR HYBRID GAIT REHABILITATION ROBOT

CROSS-REFERENCE TO RELATED APPLICATIONS

This application is a Section 371 of International Application No. PCT/KR2020/012406, filed Sep. 15, 2020, which was published in the Korean language on Apr. 1, 2021 under International Publication No. WO 2021/060759 A1, which claims priority under 35 U.S.C. § 119 to Korean Patent Application No. 10-2019-0119284, filed on Sep. 27, 2019 the disclosures of all of which are incorporated herein by reference in their entireties.

TECHNICAL FIELD

The present invention relates to a driving system and a control method for a hybrid gait rehabilitation robot. More specifically, the present invention relates to a driving system and a control method for a parallel hybrid gait rehabilitation robot that separates a gait force of a patient and a gait force of a robot.

BACKGROUND ART

In general, gait rehabilitation robots are robots used for rehabilitation treatment of patients of which movements are inconvenient due to causes such as lower extremity paralysis or decreased muscle strength.

Due to the aging, patients having representative diseases of central nervous system diseases caused by cerebral strokes are rapidly increasing. Due to decreases in exercise abilities of lower extremities that frequently occur in these patients, it may be difficult for the patients to perform various movements of daily living, such as standing, walking, and moving. Thus, there is a tendency for the development of gait rehabilitation technologies for rehabilitation treatment of the patients of which movements are inconvenient to be continuously conducted.

Currently commercialized gait rehabilitation robots have problems in popularity due to a very high volume, a very high weight, and a very high price because the patients wear robots equipped with a large number of motors or robot arms are mounted on feet.

Further, there is a disadvantage in that gait training is impossible only with forces of the patients by directly limiting the lower extremities of the patients with a robot joint.

RELATED ART DOCUMENT

Korean Patent Application Publication No. 10-2019-0046161.

DISCLOSURE

Technical Problem

The present invention is directed to providing a parallel hybrid driving unit in which a gait force of a patient and a gait force of a robot are separated from each other so that an occupant may rotate a lower extremity mechanism even when a motor is not operated and the lower extremity mechanism may rotate even when the motor is operated and the occupant does not apply a force.

The purpose of the present invention is to generate the gait force of the robot for muscle strength assistance according to a gait speed of the occupant.

The aspects of the present invention are not limited to the aspects described above and those skilled in the art will clearly understand other aspects not described herein from the following description.

Technical Solution

One aspect of the present invention provides a driving system for a hybrid gait rehabilitation robot, the driving system including a driving unit that is connected to a footrest of a gait rehabilitation robot and transmits a driving force so that the gait rehabilitation robot operates at a preset speed, a speed detection unit that detects a gait speed of an occupant, and a control unit that controls a speed of the driving unit by comparing the detected speed of the speed detection unit with a speed applied by the driving unit, wherein the driving unit transmits power to the occupant, but a driving force of the occupant is not transmitted to the driving unit.

The speed detection unit may detect the gait speed of the occupant by measuring an angular speed of a crank of a lower extremity mechanism connected to the footrest.

The driving unit may transmit the power to a pair of footrests using one rotary shaft.

The driving unit may include a free wheel body, a decelerator, and a motor, and the free wheel body may transmit a driving force of the motor to the footrest but prevents the driving force of the occupant from being transmitted from the free wheel body to the motor.

The driving unit may be driven according to a preset gait speed, and a speed of a motor may be changed according to an angle of a crank.

The control unit may control the speed of the motor by Equation 1.

$$V_{motor}=f(\theta_c)+K_p(v_{walking}-a) \quad \text{[Equation 1]}$$

($V_{MOTOR}$ denotes the speed of the motor, $f(\theta_c)$ denotes a motor speed profile function according to an angle $\theta_c$ of the crank corresponding to a reference gait speed a, $v_{walking}$ denotes a target gait speed of the occupant, $K_p$ denotes a proportional constant between the gait speed and the speed of the motor, and a denotes a preset occupant reference gait speed).

The control unit may determine the speed of the motor in consideration of a speed intention and an acceleration intention of the occupant.

The control unit may control the speed of the motor by Equation 2.

$$V_{motor}=f(\theta_c)+K_p(v_{walking}-a)+k_v(\theta_c-kg(\theta_c))+k_a(\theta''_c-kg'(\theta_c)) \quad \text{[Equation2]}$$

($V_{MOTOR}$ denotes the speed of the motor, $f(\theta_c)$ denotes a motor speed profile function according to the angle $\theta_c$ of the crank corresponding to a reference gait speed a, $v_{walking}$ denotes a target gait speed of the occupant, $K_p$ denotes a proportional constant between the gait speed and the speed of the motor, a means a preset occupant reference gait speed, $k_v$ denotes a speed intention gain, $k_a$ denotes an acceleration intention gain, k denotes a proportion constant between the speed of the motor and a speed of the crank, $$g(\theta_c)=f(\theta_c)+K_p(v_{walking}-a),\ \theta'=\frac{d\theta_c}{dt},$$

$$g'(\theta_c)=\frac{dg(\theta_c)}{dt},\text{ and }\theta''=\frac{d^2\theta_c}{dt^2}\Bigg).$$

Another aspect of the present invention provides a method of driving a hybrid gait rehabilitation robot, the method including a driving force transmitting operation of transmitting a driving force generated in a driving unit to a footrest of an occupant of a gait rehabilitation robot, a gait speed determination operation of determining a gait speed of the occupant transmitted from the footrest, an occupant intention determination operation of comparing a speed of a crank shaft of a lower extremity mechanism with a speed profile of the crank shaft set by a driving unit to determine an intention of the occupant, and a speed control operation of controlling the driving force generated in the driving unit on the basis of the intention of the occupant.

The driving unit may include a free wheel body, a decelerator, and a motor.

In the driving force transmission operation, the motor may be driven according to a preset gait training speed, and the driving force may be transmitted so that a speed of the motor is changed according to a rotation angle of the crank shaft of the lower extremity mechanism.

In the speed control operation, the speed of the motor is controlled by Equation 3.

$$V_{motor}=f(\theta_c)+K_p(v_{walking}-a) \quad \text{[Equation 3]}$$

($V_{MOTOR}$ denotes the speed of the motor, $f(\theta_c)$ denotes a motor speed profile function according to an angle $\theta_c$ of the crank corresponding to a reference gait speed a, $v_{walking}$ denotes a target gait speed of the occupant, $K_p$ denotes a proportional constant between the gait speed and the speed of the motor, and a denotes a preset occupant reference gait speed).

In the speed control operation, the speed of the motor is controlled by Equation 4.

$$V_{motor}=f(\theta_c)+K_p(v_{walking}-a)+k_v(\theta_c-kg(\theta_c))+k_a(\theta''_c-kg'(\theta_c)) \quad \text{[Equation4]}$$

($V_{MOTOR}$ denotes the speed of the motor, $f(\theta_c)$ denotes a motor speed profile function according to the angle $\theta_c$ of the crank corresponding to a reference gait speed a, $v_{walking}$ denotes a target gait speed of the occupant, $K_p$ denotes a proportional constant between the gait speed and the speed of the motor, a denotes a preset occupant reference gait speed, $k_v$ denotes a speed intention gain, $k_a$ denotes an acceleration intention gain, k denotes a proportion constant between the speed of the motor and a speed of the crank, $$g(\theta_c)=f(\theta_c)+K_p(v_{walking}-a),\ \theta'=\frac{d\theta_c}{dt},$$
$$g'(\theta_c)=\frac{dg(\theta_c)}{dt},\ \text{and}\ \theta''=\frac{d^2\theta_c}{dt^2}\bigg).$$

Advantageous Effects

According to an embodiment, since a speed of a motor is increased or decreased according to a gait speed of an occupant, long-term training can be performed due to muscle strength assistance of the occupant, thereby increasing an rehabilitation effect.

Further, by generating the speed of the motor using a gait speed pattern of a normal person, the occupant can continuously perform a normal gait exercise without the feeling of unfamiliarity.

Various and beneficial advantages and effects of the present invention are not limited to the above description, and will be more easily understood in a process of describing specific embodiments of the present invention.

DESCRIPTION OF DRAWINGS

FIG. 1 is an upper perspective view of a gait rehabilitation robot to which a driving system for a hybrid gait rehabilitation robot is applied according to an embodiment of the present invention.

FIG. 2 is a lower perspective view of FIG. 1.

FIG. 3 is a structural diagram of the driving system for the hybrid gait rehabilitation robot according to the embodiment of the present invention.

FIG. 4 is a view illustrating a configuration of a driving unit that is a component of FIG. 3.

FIG. 5 is a view illustrating a gait speed according to an angle of a crank of an occupant getting on the gait rehabilitation robot.

FIG. 6 is a view illustrating a speed of a motor of the driving unit of FIG. 3.

FIG. 7 is a view illustrating a structure in which a speed detection unit of FIG. 3 measures the angle of the crank.

FIG. 8 is a flowchart of a driving control method of a hybrid gait rehabilitation robot according to another embodiment of the present invention.

[Modes of the Invention]

Hereinafter, exemplary embodiments of the present invention will be described in detail with reference to the accompanying drawings.

However, the technical spirit of the present invention is not limited to some embodiments to be described, and may be implemented in various different forms, and one or more of components may be selectively combined or substituted between the embodiments within the scope of the technical spirit of the present invention.

Further, unless explicitly defined and described, terms (including technical and scientific terms) used in the embodiments of the present invention can be interpreted in a meaning that may be generally understood by those skilled in the art to which the present invention pertains. Terms generally used, such as terms defined in the dictionary, may be interpreted in consideration of the meaning of the context of the related technology.

Further, terms used in the embodiments of the present invention are for describing the embodiments and are not intended to limit the present invention.

In the present specification, a singular form may include a plural form unless specifically mentioned in a phrase, and when “at least one (or one or more) of A, B, and C” is described, one or more of all possible combinations of A, B, and C may be included.

Further, in the description of the components of the embodiments of the present invention, the terms such as first, second, A, B, (a), and (b) may be used.

These terms are not used to delimit an essence, an order or sequence, and the like of a corresponding component but used merely to distinguish the corresponding component from other components.

Further, when it is described that a first component is “connected” or “coupled” to a second component, the first component may be “connected” or “coupled” to the second component with a third component therebetween as well as the first component may be directly connected or coupled to the second component.

Further, when it is described that a first component is formed or disposed “above” or “below” a second component, the terms “above” and “below” include that one or more third components may be formed or arranged between the first and second components as well as the first and second components may be in direct contact with each other. Further, when the "above or below" is expressed, the "above or below" may include the meanings of a downward direction as well as an upward direction based on one component.

Hereinafter, embodiments for will be described in detail with reference to the accompanying drawings, the same or corresponding components are designated by the same reference numerals regardless of the reference numerals, and the duplicated description thereof will be omitted.

FIGS. 1 to 7 clearly illustrate only main feature parts in order to conceptually and clearly understand the present invention, and as a result, various modifications of the illustration are expected, and the scope of the present invention is not necessarily limited by specific shapes illustrated in the drawings.

FIG. 1 is an upper perspective view of a gait rehabilitation robot to which a driving system for a hybrid gait rehabilitation robot is applied according to an embodiment of the present invention, and FIG. 2 is a lower perspective view of FIG. 1.

Referring to FIGS. 1 and 2, a gait rehabilitation robot 10 used in the embodiment of the present invention may include a base plate 11, a rotary shaft 12, a connection part 13, a crank 14, a link part 15, and a footrest 16.

The base plate 11 is a plate-shaped support structure, and components of the gait rehabilitation robot 10 may be seated thereon. The shape of the base plate 11 is not limited, and the base plate 11 may be modified into any of various shapes for stably supporting a coupling structure.

The rotary shaft 12 may have one side connected to a driving unit 100 that is a component of the present invention and may transmit a driving force transmitted from the driving unit 100 to the gait rehabilitation robot 10.

In one embodiment, in the rotary shaft 12, two link parts 15 may be connected to one rotary shaft 12, and the driving unit 100 may be connected to one side of the rotary shaft 12. The driving force may be generated by the driving unit 100 to rotate the rotary shaft 12, and this driving force may be transmitted to the footrest 16 through the crank 14.

One side of the connection part 13 may be connected to the rotary shaft 12, and the other side thereof may be connected to the crank 14. The connection part 13 may transmit the driving force transmitted through the rotary shaft 12 to the crank 14. In one embodiment, a pulley or a chain may be used as the connection part 13.

The crank 14 may transmit a rotational force transmitted through the connection part 13 to the link part 15. A speed detection unit 200 that is a component of the present invention may be connected to the crank 14 to detect a speed on the basis of a rotation angle of the crank 14.

One side of the link part 15 may be connected to the crank 14, and the other side thereof may be connected to the footrest 16 so as to transmit the driving force to an occupant. The link part 15 has a structure in which a plurality of links are coupled and may allow the footrest 16 to move along the same trajectory as an actual gait trajectory. The structure or number of the links coupled in the link part 15 is not limited and may be variously modified.

The footrest 16 may be connected to an end of the link part 15, and the foot of the occupant may be fixed to the footrest 16. The shape of the footrest 16 is not limited and may be modified into any of various shapes.

FIG. 3 is a structural diagram of the driving system for the hybrid gait rehabilitation robot 10 according to the embodiment of the present invention, FIG. 4 is a view illustrating a configuration of a driving unit 100 that is a component of FIG. 3, FIG. 5 is a view illustrating a gait speed according to an angle of a crank 14 of an occupant getting on the gait rehabilitation robot 10, FIG. 6 is a view illustrating a speed of a motor of the driving unit 100 of FIG. 3, and FIG. 7 is a view illustrating a structure in which a speed detection unit 200 of FIG. 3 measures the angle of the crank 14.

Referring to FIGS. 3 to 7, a driving system for the hybrid gait rehabilitation robot 10 according to the embodiment of the present invention may include the driving unit 100, the speed detection unit 200, and a control unit 300.

The driving unit 100 may be connected to the footrest 16 of the gait rehabilitation robot 10 and may transmit the driving force so that the gait rehabilitation robot 10 operates at a preset gait training speed. When the occupant gets on the gait rehabilitation robot 10, the occupant may set a gait training speed of the gait rehabilitation robot 10 in advance, and the driving unit 100 may be driven according to the set gait training speed.

The driving unit 100 may be connected to one rotary shaft 12 and transmit power to a pair of footrests 16.

Referring to FIG. 4, the driving unit 100 may include a free wheel body 110, a decelerator 130, and a motor 150.

Since the free wheel body 110 allows unidirectional power transmission, a driving force generated by the motor 150 is transmitted to the footrest 16, and a driving force of the occupant is not transmitted to the motor 150. When the occupant performs a gait rehabilitation exercise at a higher speed than a set speed, the free wheel body 110 may be operated without being limited by the driving force of the motor 150. In the present invention, even when the occupant who needs rehabilitation does not apply a separate force, the occupant may perform gait training using the driving force of the motor 150, and when the occupant applies a force to perform rehabilitation training, a lower extremity mechanism may rotate faster without limiting driving of the motor 150.

A free wheel, which is a type of one-way clutch or overrunning clutch, is provided with a structure which is formed to transmit a rotational force only in one direction and idle in a reverse direction and in which, by making an inner ring of a double ring in the same shape as a sawtooth, a clutch cam pressed by a spring acts only in a forward direction.

The shape or type of the free wheel body 110 is not limited, and various structures for transmitting a driving force in one direction for the purpose of the present invention may be used as the free wheel body 110.

The decelerator 130 may serve to reduce a rotational speed when power generated from the motor 150 is transmitted thereto. The type of the decelerator 130 is not limited, and any of various types of the decelerators 130 such as a toothed wheel type, a fluid type, and a friction type may be used.

The motor 150 may generate the driving force transmitted to the gait rehabilitation robot 10. The motor 150 may control a speed in conjunction with the control unit 300.

Further, the driving unit 100 may be driven according to a preset speed, but the speed of the driving unit 100 may be changed according to a rotation angle of a crankshaft.

The driving unit 100 of the present invention is operated on the basis a preset speed value input by the occupant in advance. Referring to FIG. 5, a gait speed according to the angle of the crank 14 when the occupant performs the rehabilitation using the gait rehabilitation robot 10 is illustrated.

There is a speed difference between a case in which the occupant walks fast and a case in which the occupant walks slowly, but a similar type of speed change may appear according to the angle of the crank 14. A preset target training speed input by the occupant in advance during gait rehabilitation training means an average speed. However, when the speed of the driving unit 100 is controlled to be constant on the basis of the average speed, the gait speed is different from an actual rehabilitation speed according to the angle of the crank 14.

In the present invention, the driving unit 100 may generate a gait speed graph according to the angle of the crank 14 on the basis of a gait speed average value input by the occupant and may control the speed of the motor 150 in the form of a sine as illustrated in FIG. 6 on the basis of the gait speed graph. In this case, the gait speed that varies according to the angle of the crank 14 during actual rehabilitation training may be appropriately assisted, and thus rehabilitation closest to actual gait may be performed.

The speed detection unit 200 may detect the gait speed of the occupant and may transmit the detected speed information to the control unit 300.

The speed detection unit 200 may measure the angle of the crank 14 connected to the footrest 16 to measure the gait speed of the occupant. In one embodiment, the speed detection unit 200 may measure a change in the speed using an encoder.

The control unit 300 may control the speed of the driving unit 100 by comparing the detected speed of the speed detection unit 200 with a speed applied by the driving unit 100.

Even when the driving unit 100 supplies a driving force at a preset gait speed, when the occupant represents a willingness to the rehabilitation and thus the gait speed is increased, the control unit 300 may control the speed of the motor 150 of the driving unit 100 according to the increased speed.

In one embodiment, the control unit 300 may control the speed of the motor 150 by Equation 1.

$$V_{motor}=f(\theta_c)+K_p(v_{walking}-a) \quad \text{[Equation 1]}$$

($V_{MOTOR}$ denotes the speed of the motor, $f(\theta_c)$ denotes a motor speed profile function according to an angle $\theta_c$ of the crank corresponding to a reference gait speed a, $v_{walking}$ denotes a target gait speed of the occupant, $K_p$ denotes a proportional constant between the gait speed and the speed of the motor, and a denotes a preset occupant reference gait speed).

The speed of the motor 150 may be obtained in consideration of the speed of the motor according to the angle of the crank 14 and a target average gait speed of the occupant. In this case, an appropriate motor speed profile may be obtained according to the target gait speed of the occupant through a difference in the reference average gait speed a of the occupant, which is set on the basis of the target average gait speed of the occupant.

When the reference average speed value a of the occupant illustrated in FIG. 5 is 2.5 km/h and when the target gait speed of the occupant is 3.5 km/h, the control unit 300 may determine that the occupant wants to more quickly perform the rehabilitation to increase the speed of the motor 150. In this case, the speed $V_{MOTOR}$ of the motor 150 is a value of $f(\theta_c)+K_p$.

When the reference average speed value a of the occupant is 2.5 km/h and when the target gait speed of the occupant is 1.5 km/h, the control unit 300 may determine that the occupant wants to more slowly perform the rehabilitation to decrease the speed of the motor 150. In this case, the speed $V_{MOTOR}$ of the motor 150 is a value of $f(\theta_c)-K_p$.

The control unit 300 may prevent the speed of the motor 150 from being decreased according to a gait intension of the occupant according to setting, thereby continuing the rehabilitation of the occupant.

Further, in the present invention, in order to quickly detect an intention of the occupant, an acceleration as well as the speed may be considered.

In this case, the control unit 300 may determine the speed of the motor 150 in consideration of an acceleration intention of the occupant. In one embodiment, the control unit 300 may control the speed of the motor 150 by Equation 2.

$$V_{motor}=f(\theta_c)+K_p(v_{walking}-a)+k_v(\theta_c-kg(\theta_c))+k_a(\theta''_c-kg'(\theta_c)) \quad \text{[Equation2]}$$

($V_{MOTOR}$ denotes the speed of the motor, $f(\theta_c)$ denotes a motor speed profile function according to the angle $\theta_c$ of the crank corresponding to a reference gait speed a, $v_{Walking}$ denotes a target gait speed of the occupant, $K_p$ denotes a proportional constant between the gait speed and the speed of the motor, a denotes a preset occupant reference gait speed, $k_v$ denotes a speed intention gain, $k_a$ denotes an acceleration intention gain, k denotes a proportion constant between the speed of the motor and a speed of the crank, $$g(\theta_c) = f(\theta_c) + K_p(v_{walking} - a),\ \theta' = \frac{d\theta_c}{dt},$$
$$g'(\theta_c) = \frac{dg(\theta_c)}{dt},\ \text{and}\ \theta'' = \frac{d^2\theta_c}{dt^2}\Bigg).$$

In Equation 2, $f(\theta_c)+K_p(v_{walking}-a)=g(\theta_c)$ is a motor speed profile function according to a set target gait training speed $v_{walking}$.

$k_v(\theta_c-kg(\theta_c))+k_a(\theta''_c-kg'(\theta_c))$ is obtained in consideration of a gait speed intention and a gait acceleration intention of the occupant from a difference between an actual angular speed $$\left(\theta' = \frac{d\theta_c}{dt}\right)$$

of a crank shaft and a command angular speed ($kg(\theta_c)$) generated from the motor speed profile and a difference between an actual angular acceleration $$\left(\theta'' = \frac{d^2\theta_c}{dt^2}\right)$$

of the crank shaft and an angular acceleration ($kg'(\theta_c)$) generated from the motor speed profile.

Meanwhile, a method of controlling the hybrid gait rehabilitation robot 10 according to another embodiment of the present invention will be described below with reference to the accompanying drawings. However, the same description as described in the driving system for the hybrid gait rehabilitation robot 10 according to the embodiment of the present invention will be omitted.

FIG. 8 is a flowchart of a driving control method of the hybrid gait rehabilitation robot 10 according to another embodiment of the present invention. In description of FIG.

8, the same members are designated by the same reference numerals as those of FIGS. 1 to 7, and a detailed description thereof will be omitted.

Referring to FIG. 8, the driving control method of the hybrid gait rehabilitation robot 10 according to another embodiment of the present invention may include a driving force transmission operation S100, a gait speed determination operation S200, an occupant intention determination operation S300, and a speed control operation S400.

The driving force transmission operation S100 is an operation of transmitting the driving force generated in the driving unit 100 to the footrest 16 of the occupant of the gait rehabilitation robot 10. The driving unit 100 may include the free wheel body 110, the decelerator 130, and the motor 150, and using the free wheel body 110, the driving force generated by the motor 150 may be transmitted to the occupant, and in contrast, the driving force of the occupant is not transmitted to the motor 150.

In the driving force transmission operation S100, the motor 150 may be driven according to a preset speed, and the driving force may be transmitted so that the speed of the motor 150 is changed according to a rotation angle of a craft shaft connected to the footrest 16. As a result, the driving force may be transmitted close to the speed change according to a gait of the actual occupant.

In the gait speed determination operation S200, the gait speed of the occupant transmitted from the footrest 16 may be determined using the speed detection unit 200. The speed detection unit 200 may measure a speed of the footrest 16, that is, a rehabilitation speed of the occupant, through the angle of the crank 14 connected to the footrest 16.

In the occupant intention determination operation S300, the intention of the occupant during the rehabilitation may be determined by comparing a speed of the crank shaft and a speed set by the driving unit 100. In the embodiment, when the occupant performs a gait at a higher speed than the set speed, it is determined that the occupant wants to quickly perform rehabilitation exercise.

In the speed control operation S400, the driving force generated by the driving unit 100 may be controlled on the basis of the intention of the occupant. In the speed control operation S400, the driving force generated by the driving unit 100 may be adjusted through the control unit 300.

In one embodiment, in the speed control operation S400, the speed of the motor 150 may be controlled by Equation 3.

$$V_{motor}=f(\theta_c)+K_p(v_{walking}-a) \quad \text{[Equation 3]}$$

($V_{MOTOR}$ denotes the speed of the motor, $f(\theta_c)$ denotes a motor speed profile function according to an angle $\theta_c$ of the crank corresponding to a reference gait speed a, $v_{walking}$ denotes a target gait speed of the occupant, $K_p$ denotes a proportional constant between the gait speed and the speed of the motor, and a denotes a preset occupant reference gait speed).

Further, in the speed control operation S400, for precise control, the speed of the motor 150 may be controlled by Equation 4 in consideration of the acceleration intention of the occupant.

$$V_{motor}=f(\theta_c)+K_p(v_{walking}-a)+k_v(\theta_c-kg(\theta_c))+k_a(\theta''_c-kg'(\theta_c)) \quad \text{[Equation4]}$$

($V_{MOTOR}$ denotes the speed of the motor, $f(\theta_c)$ denotes a motor speed profile function according to the angle $\theta_c$ of the crank corresponding to a reference gait speed a, $v_{walking}$ denotes a target gait speed of the occupant, $K_p$ denotes a proportional constant between the gait speed and the speed of the motor, a denotes a preset occupant reference gait speed, $k_v$ denotes a speed intention gain, $k_a$ denotes an acceleration intention gain, k denotes a proportion constant between the speed of the motor and a speed of the crank, $$g(\theta_c) = f(\theta_c) + K_p(v_{walking} - a),\ \theta' = \frac{d\theta_c}{dt},$$
$$g'(\theta_c) = \frac{\mathrm{d}g(\theta_c)}{dt},\ \text{and}\ \theta'' = \frac{d^2\theta_c}{dt^2}\Big).$$

Hereinabove, the embodiments of the present invention have been described in detail with reference to the accompanying drawings.

The above description is merely illustrative of the technical spirit of the present invention, and those skilled in the art to which the present invention belongs may make various modifications, changes, and substitutes without departing from the essential features of the present invention. Thus, the embodiments disclosed in the present invention and the accompanying drawings are not intended to limit the technology spirit of the present invention, but are intended to describe the present invention, and the scope of the technical spirit of the present invention is not limited by these embodiments and the accompanying drawings. The scope of protection of the present invention should be interpreted by the appended claims, and all technical spirits within the scope equivalent thereto should be interpreted as being included in the scope of the present invention.

DESCRIPTION OF REFERENCE NUMERALS

10: Gait rehabilitation robot, 11: Base plate, 12: Rotary shaft, 13: Connection part, 14: Crank, 15: Link part, 16: Footrest, 100: Driving unit, 110: Free wheel body, 130: Decelerator, 150: Motor, 200: Speed detection unit, and 300: Control unit

The invention claimed is:

1. A driving system for a hybrid gait rehabilitation robot, the driving system comprising:

a driving unit that is connected to a footrest of a gait rehabilitation robot and transmits a driving force so that the gait rehabilitation robot operates at a preset speed;

a speed detection unit that detects a gait speed of an occupant; and a control unit that controls a speed of the driving unit by comparing the detected speed of the speed detection unit with a speed applied by the driving unit, wherein the driving unit transmits power to the occupant in a driving direction, but a driving force of the occupant in the driving direction is not transmitted to the driving unit, wherein the driving unit is driven according to a preset gait speed, and a speed of a motor is changed according to an angle of a crank, wherein the control unit determines the speed of the motor in consideration of a speed intention and an acceleration intention of the occupant, and wherein the control unit adjusts the speed of the motor by: applying a motor speed profile function based on a preset reference gait speed (a) corresponding to the angle of the crank (θc), and incorporating the difference between a target gait speed of the occupant ($v_{walking}$) and the preset reference gait speed (a) using a proportional constant between the gait speed and the motor speed, further, to reflect the occupant's speed intention, the control unit applies a speed intention gain ($k_v$) to the difference between the crank angle (θc) and a reference angle function (kg(θc)), and to reflect the occupant's acceleration intention, the control unit applies an acceleration intention gain ($k_a$) to the difference between the second derivative of the crank angle (θ"c) and the second derivative of the reference angle function (kg" (θc)), thereby finely adjusting the motor speed.

2. The driving system of claim 1, wherein the speed detection unit detects the gait speed of the occupant by measuring an angular speed of the crank of a lower extremity mechanism connected to the footrest.

3. The driving system of claim 1, wherein the driving unit transmits the power to a pair of footrests using one rotary shaft.

4. The driving system of claim 3, wherein the driving unit includes a free wheel body, a decelerator, and a motor, and the free wheel body transmits a driving force of the motor in the driving direction to the footrest but prevents the driving force of the occupant in the driving direction from being transmitted from the free wheel body to the motor.

* * * * *